(12) United States Patent
Ivashin et al.

(10) Patent No.: US 9,070,542 B2
(45) Date of Patent: Jun. 30, 2015

(54) SELECTIVE IONIZATION USING HIGH FREQUENCY FILTERING OF REACTIVE IONS

(71) Applicant: Implant Sciences Corporation, Wilmington, MA (US)

(72) Inventors: Dmitriy V. Ivashin, Peabody, MA (US); Said Boumsellek, San Diego, CA (US)

(73) Assignee: Implant Sciences Corporation, Wilmington, MA (US)

( * ) Notice: Subject to any disclaimer, the term of this patent is extended or adjusted under 35 U.S.C. 154(b) by 0 days.

(21) Appl. No.: 13/858,417

(22) Filed: Apr. 8, 2013

(65) Prior Publication Data

US 2013/0264475 A1    Oct. 10, 2013

Related U.S. Application Data

(60) Provisional application No. 61/621,210, filed on Apr. 6, 2012.

(51) Int. Cl.
*H01J 49/10* (2006.01)
*G01N 27/64* (2006.01)
(Continued)

(52) U.S. Cl.
CPC .............. *H01J 49/105* (2013.01); *H01J 49/145* (2013.01); *G01N 27/64* (2013.01); *G01N 27/624* (2013.01)

(58) Field of Classification Search
CPC .............. H01J 1/00; H01J 49/00; H01J 49/14; H01J 49/145; H01J 49/147; H01J 49/421; H01J 49/105; G01N 49/00; G01N 1/00; G01N 27/00; G01N 27/62; G01N 27/622; G01N 27/624; G01N 27/64
USPC .......................... 250/287, 282, 290, 288, 292
See application file for complete search history.

(56) References Cited

U.S. PATENT DOCUMENTS 5,245,192 A    9/1993    Houseman
5,420,424 A    5/1995    Carnahan et al.
(Continued)

FOREIGN PATENT DOCUMENTS

JP    2002289131 A    10/2002
SU    1337934 A2    9/1987

OTHER PUBLICATIONS

A.D. Appelhans and D.A. Dahl, "SIMION ion optics simulation at atmospheric pressure," *Int. J. Mass. Spectrom*, 244 (2005), pp. 1-14.
(Continued)

*Primary Examiner* — Nicole Ippolito
*Assistant Examiner* — Wyatt Stoffa
(74) *Attorney, Agent, or Firm* — Muirhead and Saturnelli, LLC

(57) ABSTRACT

Selective ionization at atmospheric or near atmospheric pressure of a sample diluted in air is provided in multiple steps. Initially, components of air and/or other gas are ionized to generate reactive ions. The reactive ions are then filtered using a high frequency filter to yield selected reactive ions. Thereafter, the selected reactive ions are reacted with sample molecules of a sample being analyzed in a charge transfer process. Depending on the properties of the sample molecules, the filter may select some reactive ions to enter the sample zone and block others entirely thus controlling ion chemistry and charge transfer yields in the sample zone. The described system is directed to controlling ions at the ion source level, using a high frequency filter technique, in connection with subsequent analysis. The method generates the ions of choice for subsequent analysis in such platforms as ion mobility and differential mobility spectrometers.

20 Claims, 5 Drawing Sheets

(51) Int. Cl.
*G01N 27/62* (2006.01)
*H01J 49/14* (2006.01)

(56) References Cited

U.S. PATENT DOCUMENTS

| | | | |
|---|---|---|---|
| 5,801,379 | A | 9/1998 | Kouznetsov |
| 5,808,416 | A | 9/1998 | Armini |
| 6,509,562 | B1 * | 1/2003 | Yang et al. .................. 250/287 |
| 6,534,765 | B1 | 3/2003 | Robb et al. |
| 6,794,645 | B2 | 9/2004 | Kanik et al. |
| 6,799,355 | B2 | 10/2004 | Guevremont et al. |
| 6,809,313 | B1 | 10/2004 | Gresham et al. |
| 6,949,739 | B2 | 9/2005 | Franzen |
| 7,119,328 | B2 | 10/2006 | Kaufman et al. |
| 7,223,967 | B2 | 5/2007 | Guevremont et al. |
| 7,299,711 | B1 | 11/2007 | Linker et al. |
| 7,368,709 | B2 | 5/2008 | Guevremont |
| 7,375,317 | B2 | 5/2008 | Zhang |
| 7,399,958 | B2 | 7/2008 | Miller et al. |
| 7,696,474 | B2 | 4/2010 | Wu et al. |
| 7,714,284 | B2 | 5/2010 | Miller et al. |
| 7,902,498 | B2 | 3/2011 | Miller et al. |
| 7,943,902 | B2 | 5/2011 | Ding et al. |
| 8,106,352 | B2 | 1/2012 | Ching |
| 8,173,959 | B1 | 5/2012 | Boumsellek et al. |
| 8,319,177 | B2 | 11/2012 | Boyle et al. |
| 8,334,505 | B2 | 12/2012 | Robinson et al. |
| 2003/0038235 | A1 | 2/2003 | Guevremont et al. |
| 2005/0001161 | A1 | 1/2005 | Hiraoka |
| 2005/0051719 | A1 * | 3/2005 | Miller et al. ................ 250/287 |
| 2005/0109930 | A1 * | 5/2005 | Hill et al. .................... 250/286 |
| 2006/0022132 | A1 * | 2/2006 | Zhang ......................... 250/290 |
| 2007/0075051 | A1 * | 4/2007 | Morrisroe ................ 219/121.52 |
| 2007/0102634 | A1 * | 5/2007 | Frey et al. .................... 250/288 |
| 2007/0176092 | A1 | 8/2007 | Miller et al. |
| 2007/0262253 | A1 * | 11/2007 | Guo et al. .................... 250/283 |
| 2008/0073502 | A1 | 3/2008 | Schneider et al. |
| 2008/0142700 | A1 | 6/2008 | Dahl et al. |
| 2008/0179515 | A1 * | 7/2008 | Sperline ...................... 250/290 |
| 2008/0237458 | A1 | 10/2008 | Wang |
| 2009/0256073 | A1 * | 10/2009 | Guo et al. .................... 250/288 |
| 2010/0207022 | A1 | 8/2010 | Tang et al. |
| 2011/0133076 | A1 | 6/2011 | Miller et al. |
| 2011/0183431 | A1 | 7/2011 | Covey et al. |
| 2012/0003748 | A1 * | 1/2012 | Robinson et al. ............. 436/173 |
| 2012/0273669 | A1 | 11/2012 | Ivashin et al. |
| 2012/0326020 | A1 | 12/2012 | Ivashin et al. |

OTHER PUBLICATIONS

I. A. Buryakov et al., "A new method of separation of multi-atomic ions by mobility at atmospheric pressure using a high-frequency amplitude-asymmetric strong electric field," International Journal of Mass Spectrometry and Ion Processes, vol. 128, Issue 3, Oct. 9, 1993, pp. 143-148.

E. V. Krylov, et al., "Selection and generation of waveforms for differential mobility spectrometry," Review of Scientific Instruments, 81, 024101 (2010), 11 pp.

* cited by examiner

250

SELECTIVE IONIZATION USING HIGH FREQUENCY FILTERING OF REACTIVE IONS

RELATED APPLICATIONS

This application claims priority to U.S. Provisional App. No. 61/621,210, filed Apr. 6, 2012, entitled "Selective Ionization," which is incorporated herein by reference.

TECHNICAL FIELD

This application is related to the field of chemical analysis and, in particular, ion mobility spectrometry.

BACKGROUND OF THE INVENTION

In field applications, chemical analysis instruments may be confronted with various complex mixtures regardless of indoor or outdoor environments. Such mixtures may cause instrument contamination and confusion due to the presence of molecular interferents producing signatures that are either identical to that of the chemical compounds of interest or unresolved by the analytical instrument due to its limited resolution. An interferent can also manifest its presence by affecting the limit of detection of the compound of interest. A multi-stage analysis approach may therefore be used to reduce the chemical noise and produce enough separation for deterministic detection and identification. The multi-stage analysis may include either a single separation technique such as mass spectrometry (MS) in $MS^n$ instruments or a combination of different separation techniques. These are called orthogonal techniques since, even though they may operate in tandem, they measure different properties of the same molecule by producing multi-dimensional spectra hence increasing the probability of detection and accuracy of detection. For field instruments, such techniques may be physically and operationally integrated in order to produce complementary information hence improving overall selectivity without sacrificing speed and sensitivity.

In the area of trace explosives detection, ion mobility spectrometry may be commonly used at passenger checkpoints in airports. The technique relies on the availability of sufficient explosives residue (particles and/or vapor) on the passenger skin, clothing, and personnel items to signal a threat. The assumption being that due to their high sticking coefficient it is difficult to avoid contamination by explosives particles during the process of handling a bomb. The same high sticking coefficient results in extremely low vapor pressures and hence makes their detection difficult. The acquisition of vapor and/or particle samples may be achieved by either swiping "suspect" surfaces of luggage or persons, or in the case of portals and/or by sending pulses of compressed air intended to liberate particles off the person's clothing, skin, shoes etc. ... In both cases the sample is introduced into an ion mobility spectrometer (IMS) for analysis.

Ion mobility spectrometry utilizes relatively low electric fields to propel ions through a drift gas chamber and separate these ions according to their drift velocity. In IMS, the ion drift velocity is proportional to the field strength and thus an ion's mobility (K) is independent of the applied field. In the IMS both analyte and background molecules are typically ionized using radioactive alpha or beta emitters and the ions are injected into a drift tube with a constant low electric field (300 V/cm or less) where they are separated on the basis of their drift velocity and hence their mobility. The mobility is governed by the ion collisions with the drift gas molecules flowing in the opposite direction. The ion-molecule collision cross section depends on the size, the shape, the charge, and the mass of the ion relative to the mass of the drift gas molecule. The resulting chromatogram is compared to a library of known patterns to identify the substance collected. Since the collision cross section depends on more than one ion characteristic, peak identification is not unique. IMS systems measure a secondary and less specific property of the target molecule—the time it takes for the ionized molecule to drift through a tube filled with a viscous gas under an electric field—and the identity of the molecule is inferred from the intensity vs time spectrum. Since different molecules may have similar drift times, IMS inherently has limited chemical specificity and therefore is vulnerable to interfering molecules.

High-field asymmetric waveform ion mobility spectrometry (FAIMS) is a detection technology which can operate at atmospheric pressure to separate and detect ions, as first described in detail by I. A. Buryakov et al., International Journal of Mass Spectrometry and Ion Processes 1993, 128 (3), pp. 143-148, which is incorporated herein by reference. FAIMS separates ions by utilizing the mobility differences of ions at high and low fields. Compared to conventional ion mobility, FAIMS operates at much higher fields (~10,000 V/cm) where ion mobilities become dependent on the applied field and are better represented by $K_h$, a non-constant high-field mobility term. Variations in $K_h$ from the low-field K, and the compound-dependence of that variation aids FAIMS in its separation power. FAIMS utilizes a combination of alternating current (AC) and direct current (DC) voltages to transmit ions of interest and filter out other ions, thus improving specificity, and decreasing the chemical noise. FAIMS can reduce false positives, since two different compounds having the same low-field mobility can often be distinguished in a high-field environment.

Ions are separated in FAIMS by their difference in mobility at high ($K_h$) and at low (K) electric fields. At a constant gas number density, N, the non-linear dependence of an ion's mobility in high electric fields can be described by $$K_h(E) = K_0 + [1 + \alpha(E/N)^2 + \beta(E/N)^4 + \ldots] \qquad \text{Eq. (1)}$$

where $K_0$ is the ion mobility coefficient at zero electric field and $\alpha$ and $\beta$ describe the dependence of the ion's mobility at a high electric field in a particular drift gas. Equation 1 is an infinite series, but at realistic field intensities the terms above the $4^{th}$ order become insignificant. FAIMS cells are commonly comprised of two parallel electrodes, one typically held at a ground potential while the other has an asymmetric waveform applied to it. A commonly used asymmetric waveform, described by V(t) in Equation 2, includes a high-voltage component (also referred to as $V_1$ or dispersion voltage [DV]) which lasts for a short period of time ($t_1$) relative to a longer lasting ($t_2$) low-voltage component ($V_2$) of opposite polarity. Most FAIMS work up to date has employed a sinusoidal wave, plus its first harmonic at twice the frequency, as shown in Equation 2, where $\omega$ is the frequency in radians per second.

$$V(t) = (0.61)V_1 \sin(\omega t) + (0.39)V_1 \sin(2\omega t - \pi 2) \qquad \text{Eq. (2)}$$

The waveform is constructed so that the voltage-time product applied to the electrode is equal to zero, as displayed in Equation 3.

$$V_1 t_1 + V_2 t_2 = 0 \qquad \text{Eq. (3)}$$

At high electric fields, the application of this waveform will cause an ion to experience a net drift toward one of the electrodes. Ions passing between the electrodes encounter this displacement because the ion's mobility during the high-voltage component ($K_h$) is different than that from the low-voltage mobility (K). In other words, the ion will move a different distance during the high-voltage portion than during the low-voltage portion. This ion will continue to migrate towards one of the electrodes and subsequently be lost unless a DC compensation voltage (CV) is applied to offset the drift. The CV values required to offset the drift of different ions will be different if the $K_h$/K ratio of the ions are different. Thus, a mixture of compounds can be successfully separated by scanning the CV, allowing each compound to transmit at its characteristic CV, creating a CV spectrum.

When higher electric fields are applied to the FAIMS electrodes, an ion can have three possible changes in ion mobility. The mobility of type A ions increases with increasing electric field strength, the mobility of type C ions decreases, and the mobility of type B ions increases initially before decreasing at yet higher fields. Most low-mass ions (<m/z 300) are type A ions, whereas most high-mass ions are type C ions.

In addition to stand-alone use, FAIMS devices may be used to filter ions prior to analyses with mass spectrometry (MS) devices and/or drift tube IMS devices, and reference is made, for example, to U.S. Patent App. Pub. No. 2010/0207022 A1 to Tang et al, entitled "Platform for Field Asymmetric Waveform Ion Mobility Spectrometry with Ion Propulsion Modes Employing Gas Flow and Electric Field," which is incorporated herein by reference. Tang et al. principally discuss multiple device instruments stages using a FAIMS device coupled to a subsequent device, such as an IMS or MS device, and in which the FAIMS device may be rapidly switched on or off to enable more sensitive analyses using the other stage(s). Tang et al. suggests that in such multiple device instrument stages it is possible for the other stage(s) to precede the FAIMS device; however, this discussion in Tang et al. is still directed towards the goal of providing a method for effective, rapid and convenient switch-off of the FAIMS separation in hybrid platforms to enable more sensitive analyses using the other stage(s).

Accordingly, it would be desirable to provide a system that provides for flexible operation to handle a variety of detection scenarios and that provides for enhanced chemical detection and identification capabilities.

SUMMARY OF THE INVENTION

According to the system described herein, a selective ionization device includes an ionization zone in which reactive ions are generated, the reactive ions being generated from a gas that is separate from a sample being analyzed and a sample zone that contains the sample being analyzed. A high frequency filter receives the reactive ions propelled from the ionization zone and delivers selected reactive ions to the sample zone. The reactive ions from the ionization zone are selectively filtered via control of electrodes of the high frequency filter generate the selected reactive ions. In the sample zone, the selected reactive ions react with the sample molecules of the sample being analyzed in a charge transfer process. The high frequency filter may include a high field asymmetric waveform ion mobility spectrometer (FAIMS). An analysis platform may be provided that analyzes sample ions of interest following the charge transfer process. The electrodes of the high frequency filter may be controlled according to mobility of the selected reactive ions and may be controlled by applying DC voltages to the filter. The electrodes of the high frequency filter may have a planar or a non-planar geometry, and the gas may be air.

According further to the system described herein, a method for selective ionization includes generating reactive ions in an ionization zone, the reactive ions being generated from a gas that is separate from a sample being analyzed. The sample being analyzed is provided in a sample zone. The method includes selectively filtering the reactive ions propelled from the ionization zone to generate selected reactive ions. The reactive ions from are selectively filtered via control of electrodes of the high frequency filter generate the selected reactive ions. In the sample zone, the selected reactive ions react with the sample molecules of the sample being analyzed in a charge transfer process. The high frequency filter may include a high field asymmetric waveform ion mobility spectrometer (FAIMS). An analysis platform may be provided that analyzes sample ions of interest following the charge transfer process. The electrodes of the high frequency filter may be controlled according to mobility of the selected reactive ions and may be controlled by applying DC voltages to the filter. The electrodes of the high frequency filter may have a planar or a non-planar geometry, and the gas may be air.

According further to the system described herein, a non-transitory computer readable medium stores software for selective ionization processing. The software includes executable code that controls generation of reactive ions in an ionization zone, the reactive ions being generated from a gas that is separate from a sample being analyzed. Executable code is provided that controls selective filtering, at a high frequency filter, of the reactive ions received from the ionization zone and controls delivery of the selected reactive ions to the sample zone. The reactive ions are selectively filtered via control of electrodes of the high frequency filter to generate the selected reactive ions. In the sample zone, the selected reactive ions react with the sample molecules of the sample being analyzed in a charged transfer process. Executable code is provided that controls analysis of sample ions of interest following the charge transfer process. The high frequency filter may include a high field asymmetric waveform ion mobility spectrometer (FAIMS). An analysis platform may be provided that analyzes sample ions of interest following the charge transfer process. The electrodes of the high frequency filter may be controlled according to mobility of the selected reactive ions and may be controlled by applying DC voltages to the filter. The electrodes of the high frequency filter may have a planar or a non-planar geometry, and the gas may be air.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

Figure 1:
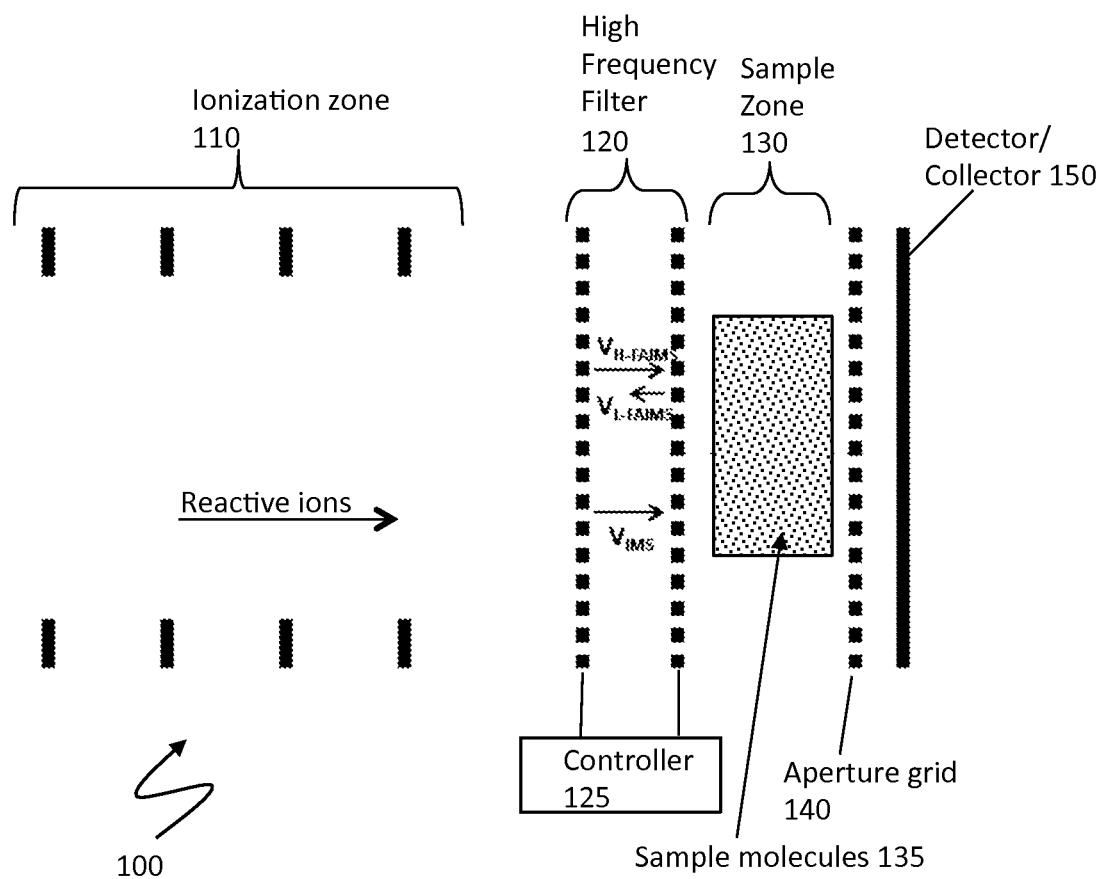
FIG. 1 is a schematic illustration showing a high frequency reactive ion filtering device according to an embodiment of the system described herein.

The system described herein provides for use of combined techniques, such as low and high field mobility techniques, to offer several advantages including low cost, no vacuum required, and the generation of 2-D spectra for enhanced detection and identification. Operation of the analytical devices may provide a system with advantageous flexibility by allowing adaptation of the hyphenated instrument to the application's requirements. With the IMS-FAIMS hardware level flexibility, the instruments may be configured and optimized to exploit different trade-offs suitable for a variety of detection scenarios for different lists of target compounds.

In an embodiment, the system described herein may be used in connection with tandem instruments using a variable frequency pulsed ionization source and two separation techniques, such as low and high field mobility. It is noted that, in various embodiments, the IMS and FAIMS devices may be orthogonal to each other, specifically in which the flow directions of ions in the IMS and FAIMS devices are orthogonal, and/or the FAIMS device may be embedded in the IMS device and in which the flow directions of ions may be co-axial along the IMS and FAIMS devices. The FAIMS cell may include two parallel grids (e.g., planar and/or non-planar grids) of approximately the same diameter as the IMS rings and can be placed anywhere along a drift tube and biased according to their location in the voltage divider ladder to create the same IMS field. The spacing between the grids constitutes the analytical gap where ions are subject, in addition to the drift field, to the asymmetric dispersive field of the FAIMS. The oscillatory motion performed during the high and low voltages of the asymmetric waveform separates the ions according to the difference in their mobilities.

As discussed elsewhere herein, it has been noted that there are synergistic benefits in combining analytical instruments. The chemical information obtained and the characteristics of the measurements are improved by more than the individual results put together. Various combinations include instruments performing the separation in either similar or different time domains and measuring the same or different properties of the species to be analyzed. Hyphenated (Instrument A/Instrument B) platforms such as Gas Chromatography (GC)-Mass Spectrometry (MS) and Ion Mobility Spectrometry (IMS)-MS are examples whereby instrument B can generate several spectra during the separation performed using instrument A. The combination of instruments A and B is mutually beneficial since the information generated by system A is enriched by system B, and system B benefits form the pre-separation performed by system A hence reducing the chemical noise. In the case of instruments operating in similar time domains the two separations can occur sequentially, whereby instrument A serves as a pre-screener and instrument B as a confirmer. In such a scenario the mode of operation of instrument A can be optimized in order to optimally exploit the trade-offs between overall sensitivity and selectivity. Reference is made to U.S. Pat. No. 8,173,959 to S. Boumsellek et al., entitled "Real-Time Trace Detection by High Field and Low Field Ion Mobility and Mass Spectrometry," which is incorporated herein by reference.

For specific descriptions of features and uses of instruments that include one or more FAIMS devices and that may be used in connection with ion detection and chemical analysis techniques, reference is made to U.S. Patent App. Pub. No. 2012/0273669 A1 to Ivashin et al., entitled "Chemical Analysis Using Hyphenated Low and High Field Ion Mobility" and U.S. Patent App. Pub. No. 2012/0326020 A1 to Ivashin et al., entitled "Ion Mobility Spectrometer Device with Embedded FAIMS," which are both incorporated herein by reference.

According to the system described herein, selective ionization at atmospheric or near atmospheric pressure of a sample (analyte) diluted in air may be provided in multiple steps. Initially, components of air (and/or other appropriate gas or medium), i.e. without sample molecules, may be ionized to generate reactive ions. The reactive ions may then be filtered using a high frequency filter, as further discussed in detail herein, to yield selected reactive ions. Thereafter, the selected reactive ions may be reacted with sample molecules of a sample being analyzed in a charge transfer process. In various embodiments, references to the charge transfer process, as provided herein, refers to the transfer of charge from the selected reactive ions directly to sample molecules and/or refers to the attaching of the selected reactive ions to sample molecules to form molecular adducts or fragments via the attachment process and/or the dissociative attachment process.

Depending on the properties of the sample molecules, the filter may select some reactive ions to enter the sample zone and block others entirely thus controlling ion chemistry and charge transfer yields in the sample zone. By scanning the filter 2-D spectra may be generated as different classes of sample ions are formed for subsequent analysis. The system described herein is thereby directed to controlling ions at the ion source level, using a high frequency filter technique, in connection with subsequent analysis. The method of the system described herein may thereby be used to generate the ions of choice for subsequent analysis in such platforms as ion mobility and differential mobility spectrometers.

FIG. 1 is a schematic illustration showing a high frequency reactive ion filtering device 100 according to an embodiment of the system described herein. The device 100 includes an ionization zone 110 in which reactive ions are generated. The reactive ions may be ionized components of air and/or other gas that is separate from a sample being analyzed. A high frequency filter 120 is positioned between the ionization zone 110 and a sample zone 130 that includes sample molecules of the sample being analyzed and which is charge transfer occurs between the ions from the high frequency filter 120 and the sample molecules 135. From the sample zone 130, ions of interest may travel through an aperture grid 140 to a detector/collector assembly 150 for analysis according to an embodiment of the system described herein.

The high frequency filter 120 can be used in connection with various ionization methods in the ionization zone 110, including corona, photonic, and radioactive sources. The high frequency filter 120 may include a cell made of two parallel grids of various shapes, including cylindrical, spherical, and planar. In an embodiment, the filter may be a FAIMS cell. Within the cell, in the analytical gap between the parallel grids, the combination of drift and high frequency asymmetric axial fields is applied. The high frequency field alternates between high and low fields and subjecting ions to oscillations within the cell. Ions are either accelerated or decelerated depending on the nature of their high field mobility. Applying a small DC voltage can filter out specific ions on the basis of differences between their low and high field mobilities. The high frequency filter 120 is shown situated between the ionization zone 110 where the reactive ions are formed and the sample zone 130 where charge transfer occurs. By applying specific DC voltages, controlled by a controller 125, the high frequency filter may be used to control which reactive ions enter the sample zone 130 and which do not. Using such a filter, which can be adapted according to the properties of the sample molecules, one is able to control charge transfer yields in the sample zone. This method can be used to generate the ions of choice for subsequent analysis in such platforms as ion mobility and differential mobility spectrometers.

In other embodiments, as further discussed elsewhere herein, it is noted that the high frequency filter 120 may be mounted within the ionization zone 110, for example, somewhere along a length of an IMS drift tube of the ionization zone from which ions are drifting after ionization by an ionization source (not shown). In other embodiments, more than one high frequency filter 102 may be used in connection with the system described herein.

As noted, the FAIMS cell of the high frequency filter 120 may have a planar geometry design and/or other non-planar geometry design, including cylindrical, spherical, and/or other appropriate geometries. Reference is made, for example, U.S. Pat. No. 7,368,709 to Guevremont, entitled "Low field mobility separation of ions using segmented cylindrical FAIMS" and U.S. Pat. No. 7,223,967 to Guevremont et al., entitled "Side-to-side FAIMS apparatus having an analyzer region with non-uniform spacing and method therefore," which are incorporated herein by reference, and provide discussion of FAIMS devices having non-planar geometries, among other FAIMS concepts.

Between the parallel plates or grids of a FAIMS cell, ions are subject to two orthogonal forces: (1) a dispersive force due the high frequency asymmetric field moving the ions towards either plate; and (2) a longitudinal force moving the ions from the entrance to the exit of the cell. The longitudinal force can be either pneumatic or electrostatic. FAIMS devices may feature gas flows established by pumps to pneumatically carry the ions through the cell. Such devices are called flow-driven FAIMS and require a number of additional considerations. For example, a mechanism may be required to separate the carrier gas from the ions to avoid additional chemical reactions outside the ionization source. Further, the ions acquire the local gas flow velocity during their transit through the cell. Such velocity has a parabolic profile across the gap meaning ions moving near the gap median are faster than ions moving near the plates. This leads to a distribution of residence times of the same species causing a reduction of the effective gap and therefore a loss of sensitivity. Additionally, pumps may be required to draw a sample medium into the FAIMS cell and to provide a carrier gas can be rather large and consume large amounts of power. The carrier gas should flow in the same direction as the ions, requiring a structure which separates the analytical gap from the ionization source.

In contrast, in field-driven FAIMS devices, ions are electrostatically propelled through the cell using segmented electrodes, for example. Such devices can more quickly and accurately control the flow of selected ions to produce a sample spectrum. According to the system described herein, upon entering the FAIMS cell of the high frequency filter 1020, the ions are subject to the forces of the asymmetric field making them oscillate along the axis of the ionization zone. Depending on the value of the mobility at high fields compared to that at low fields (some ions have higher mobility, some have lower mobility), the ions will either be accelerated or decelerated through the FAIMS cell, thus causing a shift in their respective drift times, which is advantageously used to separate and detect desired ions of interest. It is noted that the system described herein that may be used with FAIMS cells having planar and/or non-planar geometries, as further discussed elsewhere herein.

Ion velocities within the high frequency filter 120 are illustrated in the figure according to an embodiment of the system described herein. Ions are propelled from the ionization zone 110 to the FAIMS cell of the high frequency filter 120. Within the FAIMS cell, the ions are subject to electrostatic forces. $V_{ims}$ is the ion velocity due to the IMS field of the ionization zone that may propel the ions through the device 100. The controller 125 may control the field generated between the plates of the FAIMS cell according to the high field asymmetric waveform operation of the system described herein. $V_{FAIMS}$ is the net velocity of the ions due to the asymmetric waveform. $V_{FAIMS}$ may be calculated according to Equation 4:

$$V_{FAIMS} = V_{H\text{-}FAIMS} - V_{L\text{-}FAIMS} = K_H E_H - K_L E_L \quad \text{Eq. (4)}$$

where $V_{H\text{-}FAIMS}$ is the velocity and $K_H$ the mobility during the high field ($E_H$) and $V_{L\text{-}FAIMS}$ the velocity and $K_L$ the mobility during the low field ($E_L$).

Figure 2:
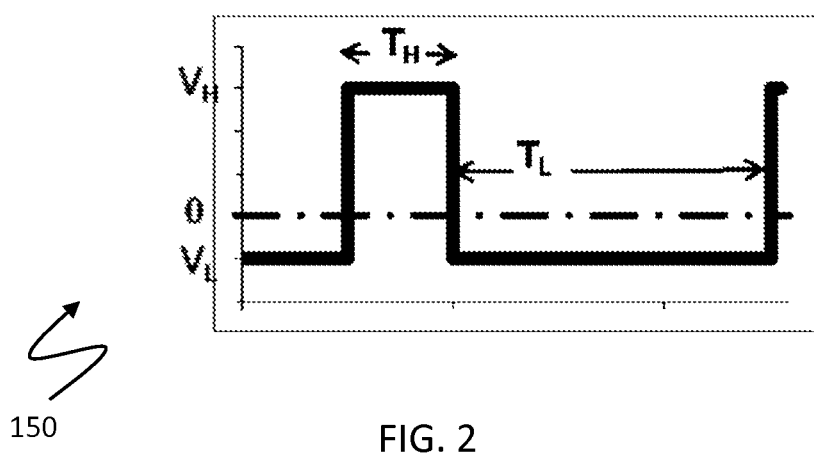
FIG. 2 is a plot showing parameters of an asymmetric waveform that may be used in connection with an embodiment of the system described herein.

The flight time through the FAIMS cell $T_{cell}$ is governed by the IMS field as well as the oscillations due to the FAIMS field. $T_{cell}$ can be derived from the following:

$$1/T_{cell} = 1/T_{IMS} + E_H T_H (K_H - K_L)/W \cdot (T_H + T_L) \quad \text{Eq. (5)}$$

$$T_{IMS} = W/K \cdot E_{IMS} \quad \text{Eq. (6)}$$

where W is the width of the cell, K is the IMS mobility, $T_H$ and $T_L$ are the duration of the high and low fields within the asymmetric waveform (see FIG. 2).

FIG. 2 is a plot 150 showing parameters of an asymmetric waveform that may be used in connection with an embodiment of the system described herein. $T_H$ and $T_L$ show the duration of the high and low fields within the asymmetric waveform. Depending on the polarity of the waveform and the polarity of the difference between the high field and low field mobilities, $T_{cell}$ is either shorter or longer than $T_{IMS}$. Assuming the analysis of negative ions and assuming a positive waveform (the high field segment is positive while the low field segment is negative), type A ions (larger mobility at higher fields) move slower through the cell while type C ions move faster through the cell causing a few ms shifts in the IMS spectrum. Other FAIMS parameters that affect the transit time in the cell include the high field $E_H$ and the duty cycle of the asymmetric waveform $T_H/(T_H+T_L)$.

The shape of a drive waveform for a FAIMS cell of the high frequency filter is one of the features affecting FAIMS' resolution, transmission, and separation. Due to practical circuitry advantages, FAIMS cells often employ a waveform formed by summing a sinusoidal wave and its first harmonic, at twice the frequency, resulting in first order Fourier approximation of an asymmetric square wave. It is noted that a rectangular drive waveform may be advantageous for FAIMS analyses. Analytical considerations show that rectangular waveforms may improve ion separation efficiency, resolution and/or sensitivity as compared to sinusoidal waveforms. Intuitively, use of an asymmetric square (and/or other rectangular) waveform for FAIMS would seem to maximize the differences during the high and low field portions of the electric field. These high to low periods of the waveform permit an ion to experience a maximum of unequal voltages maximizing the CV. However, in previous studies, there have been concerns that the time it takes an ion to respond to the idealized asymmetric square waveform and reach "steady state," or terminal, drift velocity might be sufficiently long to introduce error due to the transient electric field. It has been shown that, to the first order, this can be neglected if the time for reaching terminal velocity is small relative to the total drift time. Since the estimated time necessary to reach this velocity in a transient electric field is in the picosecond range and the drift time is in the millisecond range, this factor can therefore be ignored. In connection with generating waveforms for use with the system described herein, reference is made to, for example, E. V. Krylov, et al., "Selection and generation of waveforms for differential mobility spectrometry," Review of Scientific Instruments, 81, 024101 (2010), 11 pp., which is incorporated herein by reference.

The asymmetric waveform features a high voltage component causing the ion mobility to change with the field. As a consequence, a net change in the velocity of the ions, characteristic of the analyzed ions, results from the oscillations between high and low fields. Such a net change in the velocity may be either positive or negative for different ions. Depending on the nature of the mobility of the ions at high fields compared to that at low fields, the ions will either be accelerated or decelerated through the cell (and even including being stopped), thus causing the shift in their respective drift times that enables the desired ion separations for purposes of measurement. Accordingly, the high frequency filter 120, provided with a stream of ions obtained by operating an ionization source, may serve as a gate filtering ions or classes of ions depending on the value of a DC voltage (called compensation voltage) applied to either one of the FAIMS grids. Scanning such a DC voltage generates a spectrum.

Figure 3A:
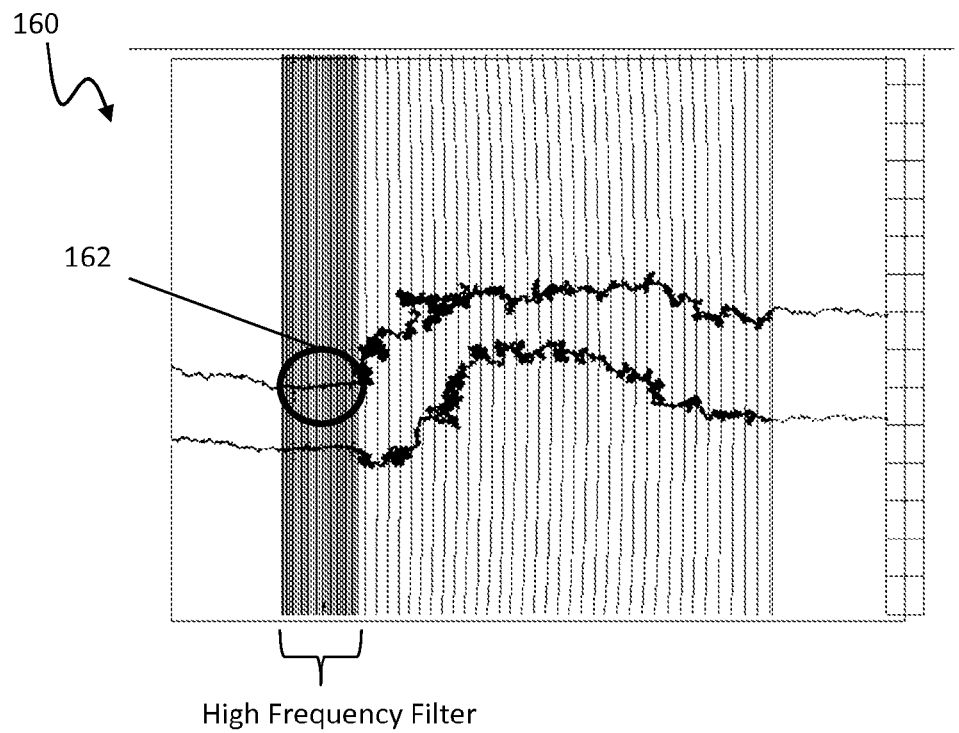
FIG. 3A is an illustration showing an example of trajectories of ions through the FAIMS cell of the high frequency filter towards the sample zone.
Figure 3B:
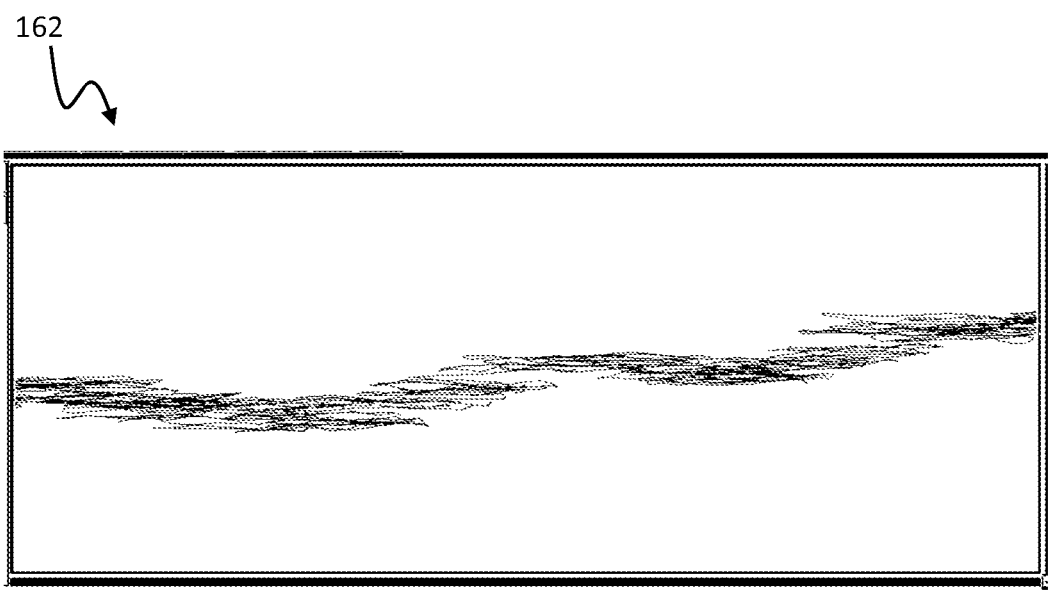
FIG. 3B is an enlarged view of the demarcated area shown in FIG. 3A showing ion oscillations due to the high frequency dispersive field and a resulting net change in velocity of the ions.

FIG. 3A is an illustration 160 showing an example of trajectories of ions through the FAIMS cell of the high frequency filter 120 towards the sample zone 130. In an embodiment, the embedded FAIMS cell of the high frequency filter 120 is field-driven. FIG. 3B is an enlarged view of the demarcated area 162 shown in FIG. 3A showing ion oscillations due to the high frequency dispersive field and a resulting net change in velocity of the ions. Upon entering the FAIMS cell, the ions experience both a mobility due to the low IMS field and oscillations due to the high frequency of the asymmetric waveform of the dispersion voltage. It is noted that the figures also show a slight radial displacement of the ions that may result from diffusion effects at atmospheric pressure rather than being due to the electrical forces of the asymmetric field, at least for ions closer to the main axis where fringing fields are negligible.

Ion trajectories may be calculated using known techniques. For example, ion trajectories may be calculated using the Simion ray tracing package. A user program called Statistical Diffusion Simulation (SDS) is invoked by Simion to model the ion motion at atmospheric pressure. Reference is made to A. D. Appelhans and D. A. Dahl, "SIMION ion optics simulation at atmospheric pressure," *Int. J. Mass. Spectrom,* 244 (2005), pp. 1-14, which is incorporated herein by reference. The SDS code takes into account effects of high pressure collisions by modeling both diffusional and mobility terms of ions in a neutral gas. Ion dynamics are simulated by combined viscous ion mobility and random ion jumping (diffusion) approach. Space charge effects are not included in the SDS package and may be treated separately, for example, using the Coulomb Repulsion feature built into Simion.

Figure 4:
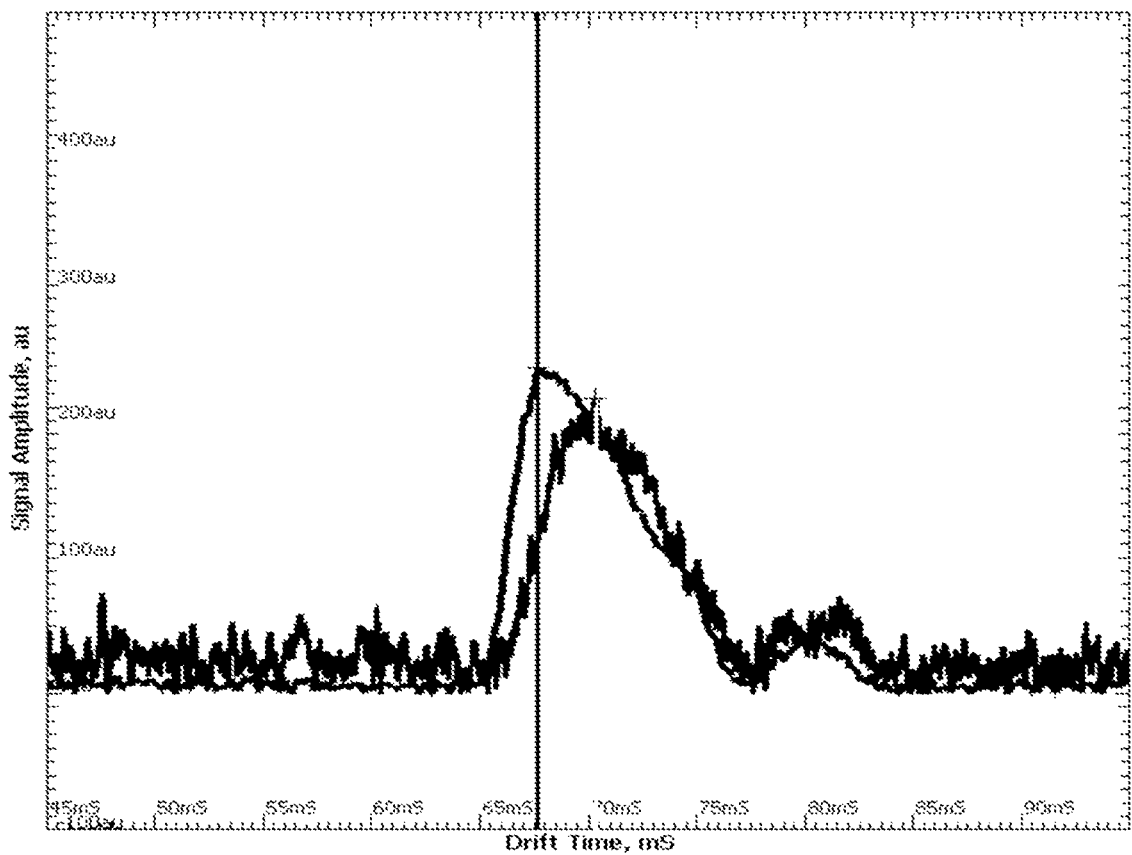
FIG. 4 is a plot of drift time (ms) along the x-axis and signal amplitude (au) along the y-axis that may be used in connection with an embodiment of the system described herein.
Figure 4:

FIG. 4 is a plot 200 of drift time (ms) along the x-axis and signal amplitude (au) along the y-axis that may be used in connection with an embodiment of the system described herein. The plot shows about a 2.75 ms shift to the right upon applying the high frequency dispersion voltage in the FAIMS cell of the high frequency filter 120 according to an embodiment of the system described herein. As discussed, by performing oscillations within the FAIMS cell, ions are either accelerated or decelerated depending on whether the high field mobility (KH) is higher (type A) or lower (type C). Upon applying the high frequency field shifts along the drift time axis, various amounts of shifts depending on the compounds are observed with the reactive ions. This represents an additional dimension for separation that combines low and high properties of the mobility of the species into the same spectrum. As illustrated and noted, assuming the analysis of negative ions and assuming a positive waveform (the high field segment is positive while the low field segment is negative), type A ions (larger mobility at higher fields) move slower through the cell while type C ions move faster through the cell causing a few ms (2.75, as shown) shift in the IMS spectrum.

Figure 5:
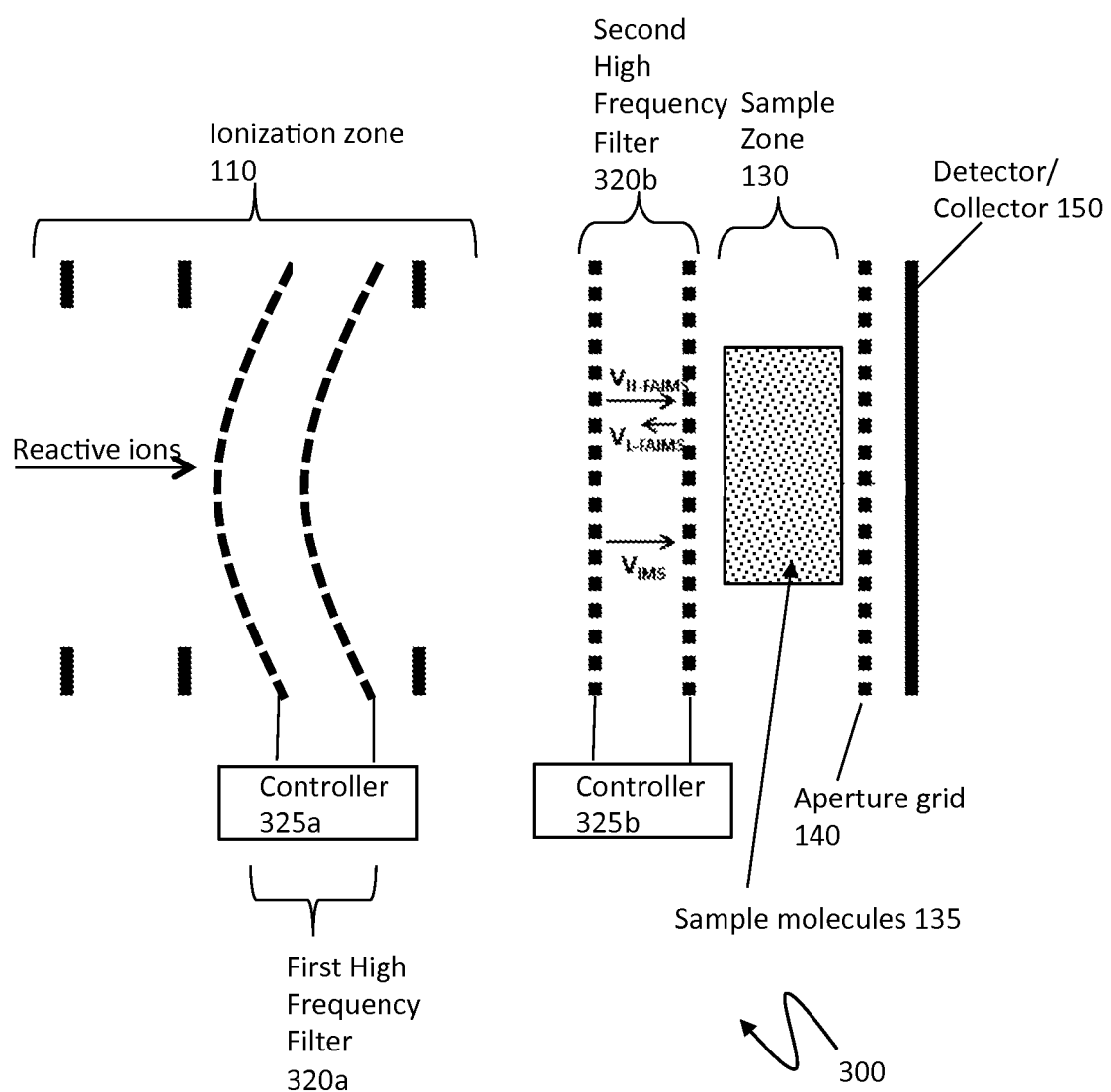
FIG. 5 is a schematic illustration showing a high frequency reactive ion filtering device having showing multiple high frequency filters according to an embodiment of the system described herein.

FIG. 5 is a schematic illustration showing a high frequency reactive ion filtering device 300 according to an embodiment of the system described herein, having components like that shown and described in connection with the device 100, but further showing multiple high frequency filters 321 and 322. Although two high frequency filters 321, 322 are illustrated, it is noted that more than two high frequency filters may also be used in connection with the system described herein. In the illustrated example, the first high frequency filter 320a is shown having a non-planar geometry (e.g., crescent-shaped electrodes) and the second high frequency filter 320b is shown having a planar geometry (e.g., plate electrodes).

It is noted that the high frequency filter 320a is shown positioned in the ionization zone 110 which, for example, may be somewhere along a length of an IMS drift tube of the ionization zone from which ions are drifting after ionization by an ionization source (not shown). By having multiple high frequency filters 320a,b the time shifts of ions moving through device 300 may be enhanced thereby further improving operation of the system to separate and detect desired ions of interest. As shown each of the filters 320a,b may be controlled by controllers 325a,b, that, although illustrated separately, may be a single controller.

Figure 6:
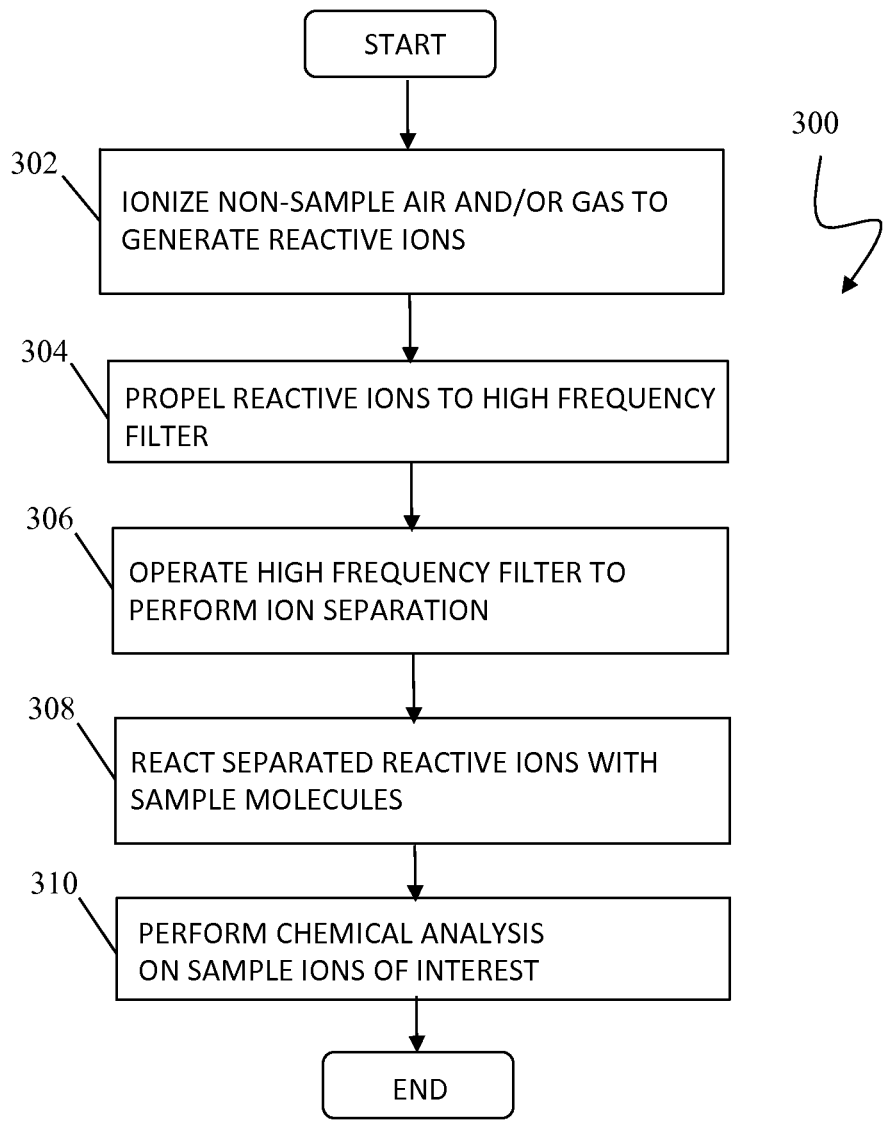
FIG. 6 is a flow diagram showing selective ionization processing steps using a high frequency filter according to an embodiment of the system described herein.

FIG. 6 is a flow diagram 300 showing selective ionization processing steps using a high frequency filter according to an embodiment of the system described herein. In an embodiment, it is noted that the selective ionization may be performed at atmospheric or near atmospheric pressure. At a step 302, components of a non-sample gas (e.g., air and/or other appropriate gas) may be ionized by an ionization source to generate reactive ions in an ionization zone. After the step 302, processing proceeds to a step 304, where the reactive ions are propelled from the ionization zone to a high frequency filter. After the step 304, processing proceeds to a step 306 where the high frequency filter is operated to separate at least some of the reactive ions, as further discussed elsewhere herein, involving the use of oscillations of the ions and in which the direction of the generated oscillations is co-axial with the direction of the propelled ions through the drift tube. The oscillations cause a net change in velocity of at least some ions moving along the axial direction of the drift tube. As discussed elsewhere herein, depending on the nature of the mobility of the ions at high fields compared to that at low fields, the ions will either be accelerated or decelerated through the cell (and even including being stopped), thus causing the shift in their respective drift times that enables the desired ion separations for purposes of measurement.

After the step 306, processing proceeds to a step 308, where selected reactive ions, as according to operation of the high frequency filter, are reacted with sample molecules of a sample being analyzed in a charge transfer process. As discussed elsewhere herein, the charge transfer process may include direct transfer of charge form the selected reactive ions to the sample molecules and/or may include attachment of the selected reactive ions to sample molecules to form molecular adducts or fragments via the attachment process and/or the dissociative attachment process. After the step 308, processing proceeds to a step 310 where chemical analysis is performed on the generated sample ions of interest in such platforms as ion mobility and differential mobility spectrometers. After the step 310, processing is complete.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. Software implementations of the system described herein may include executable code that is stored in a computer readable medium and executed by one or more processors. The computer readable medium may include a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A selective ionization device, comprising:
an ionization zone in which reactive ions are generated, the reactive ions being generated from a gas that is separate from a sample being analyzed;
a sample zone that contains the sample being analyzed; and
a high frequency filter that receives the reactive ions propelled from the ionization zone and delivers selected reactive ions to the sample zone wherein the reactive ions from the ionization zone are selectively filtered via control of electrodes of the high frequency filter to generate the selected reactive ions, wherein the electrodes are controlled via an asymmetric waveform alternating between high and low fields that subjects the reactive ions to oscillations within the high frequency filter resulting in separation of the reactive ions based on differences between high field and low field mobilities of the reactive ions, wherein a compensation voltage is further applied to then deliver the selected reactive ions from the high frequency filter, wherein, in the sample zone, the selected reactive ions react with the sample molecules of the sample being analyzed in a charge transfer process at atmospheric or near atmospheric pressure.

2. The selective ionization device according to claim 1, wherein the high frequency filter includes a high field asymmetric waveform ion mobility spectrometer (FAIMS).

3. The selective ionization device according to claim 1, further comprising:
an analysis platform that analyzes sample ions of interest following the charge transfer process.

4. The selective ionization device according to claim 1, wherein the electrodes of the high frequency filter have a planar or a non-planar geometry.

5. The selective ionization device according to claim 1, wherein the gas is air.

6. The selective ionization device of claim 1, wherein the reactive ions are propelled through the high frequency filter by an ion mobility spectrometer (IMS) field that is separate from the fields generated by the asymmetric waveform of the high frequency filter that causes the oscillations of the reactive ions.

7. The selective ionization device of claim 6, wherein the separation of the reactive ions is controlled based on a flight time ($T_{cell}$) of a particular ion of the reactive ions through the high frequency filter, the flight time ($T_{cell}$) being determined according to the following equations:

$$1/T_{cell} = 1/T_{IMS} + E_H T_H (K_H - K_L)/W \cdot (T_H + T_L)$$

$$T_{IMS} = W/K \cdot E_{IMS}$$

where $K_H$ is a mobility of the particular ion during a high field ($E_H$) generated by the asymmetric waveform, $K_L$ is a mobility of the particular ion during a low field ($E_L$) generated by the asymmetric waveform, $T_H$ is a duration of the high field within the asymmetric waveform, $T_L$ is a duration of the low field within the asymmetric waveform, $T_{IMS}$ is a non-oscillating transmit time of the particular ion through the high frequency filter, W is a width of the high frequency filter, and K is a mobility of the particular ion in the IMS field ($E_{IMS}$).

8. A method for selective ionization, comprising:
generating reactive ions in an ionization zone, the reactive ions being generated from a gas that is separate from a sample being analyzed;
providing the sample being analyzed in a sample zone;
selectively filtering the reactive ions propelled from the ionization zone to generate selected reactive ions, wherein the reactive ions from the ionization zone are selectively filtered via control of electrodes of the high frequency filter to generate the selected reactive ions, wherein the electrodes are controlled via an asymmetric waveform alternating between high and low fields that subjects the reactive ions to oscillations within the high frequency filter resulting in separation of the reactive ions based on differences between high field and low field mobilities of the reactive ions, wherein a compensation voltage is further applied to then deliver the selected reactive ions from the high frequency filter; and
in the sample zone, reacting the selected reactive ions with the sample molecules of the sample being analyzed in a charge transfer process at atmospheric or near atmospheric pressure.

9. The method according to claim 8, wherein the high frequency filter includes a high field asymmetric waveform ion mobility spectrometer (FAIMS).

10. The method according to claim 8, further comprising:
analyzing sample ions of interest following the charge transfer process.

11. The method according to claim 8, wherein the electrodes of the high frequency filter have a planar or a non-planar geometry.

12. The method according to claim 8, wherein the gas is air.

13. The method of claim 8, wherein the reactive ions are propelled through the high frequency filter by an ion mobility spectrometer (IMS) field that is separate from the fields generated by the asymmetric waveform of the high frequency filter that causes the oscillations of the reactive ions.

14. The method of claim 13, wherein the separation of the reactive ions is controlled based on a flight time ($T_{cell}$) of a particular ion of the reactive ions through the high frequency filter, the flight time ($T_{cell}$) being determined according to the following equations:

$$1/T_{cell} = 1/T_{IMS} + E_H T_H (K_H - K_L)/W \cdot (T_H + T_L)$$

$$T_{IMS} = W/K \cdot E_{IMS}$$

where $K_H$ is a mobility of the particular ion during a high field ($E_H$) generated by the asymmetric waveform, $K_L$ is a mobility of the particular ion during a low field ($E_L$) generated by the asymmetric waveform, $T_H$ is a duration of the high field within the asymmetric waveform, $T_L$ is a duration of the low field within the asymmetric waveform, $T_{IMS}$ is a non-oscillating transmit time of the particular ion through the high frequency filter, W is a width of the high frequency filter, and K is a mobility of the particular ion in the IMS field ($E_{IMS}$).

15. A non-transitory computer-readable medium storing software for selective ionization processing, the software comprising:
   executable code that controls generation of reactive ions in an ionization zone, the reactive ions being generated from a gas that is separate from a sample being analyzed;
   executable code that controls selective filtering, at a high frequency filter, of the reactive ions received from the ionization zone and controls delivery of the selected reactive ions to the sample zone, wherein the reactive ions are selectively filtered via control of electrodes of the high frequency filter to generate the selected reactive ions, wherein the electrodes are controlled via an asymmetric waveform alternating between high and low fields that subjects the reactive ions to oscillations within the high frequency filter resulting in separation of the reactive ions based on differences between high field and low field mobilities of the reactive ions, wherein a compensation voltage is further applied to then deliver the selected reactive ions from the high frequency filter, and wherein, in the sample zone, the selected reactive ions react with the sample molecules of the sample being analyzed in a charge transfer process at atmospheric or near atmospheric pressure; and
   executable code that controls analysis of sample ions of interest following the charge transfer process.

16. The non-transitory computer-readable medium according to claim 15, wherein the high frequency filter includes a high field asymmetric waveform ion mobility spectrometer (FAIMS).

17. The non-transitory computer-readable medium according to claim 15, wherein the electrodes of the high frequency filter have a planar or a non-planar geometry.

18. The non-transitory computer-readable medium according to claim 15, wherein the gas is air.

19. The non-transitory computer-readable medium according to claim 15, wherein the reactive ions are propelled through the high frequency filter by an ion mobility spectrometer (IMS) field that is separate from the fields generated by the asymmetric waveform of the high frequency filter that causes the oscillations of the reactive ions.

20. The non-transitory computer-readable medium according to claim 19, wherein the separation of the reactive ions is controlled based on a flight time ($T_{cell}$) of a particular ion of the reactive ions through the high frequency filter, the flight time ($T_{cell}$) being determined according to the following equations:

$$1/T_{cell} = 1/T_{IMS} + E_H T_H (K_H - K_L)/W \cdot (T_H + T_L)$$

$$T_{IMS} = W/K \cdot E_{IMS}$$

where $K_H$ is a mobility of the particular ion during a high field ($E_H$) generated by the asymmetric waveform, $K_L$ is a mobility of the particular ion during a low field ($E_L$) generated by the asymmetric waveform, $T_H$ is a duration of the high field within the asymmetric waveform, $T_L$ is a duration of the low field within the asymmetric waveform, $T_{IMS}$ is a non-oscillating transmit time of the particular ion through the high frequency filter, W is a width of the high frequency filter, and K is a mobility of the particular ion in the IMS field ($E_{IMS}$).

* * * * *